(12) United States Patent
Haupt et al.

(10) Patent No.: US 7,257,986 B2
(45) Date of Patent: Aug. 21, 2007

(54) GAS SENSOR WITH INCREASED MEASURING SENSITIVITY

(75) Inventors: Stephan Haupt, Lübeck (DE); Michael Sick, Timmendorfer Strand (DE); Rigobert Chrzan, Oldesloe (DE); Andreas Nauber, Lübeck (DE); Dieter Krüger, Stockelsdorf (DE); Christoph Bernstein, Lübeck (DE); Wilfried Diekmann, Lübeck (DE)

(73) Assignee: Dräger Safety AG & Co. KGaA (DE)

( * ) Notice: Subject to any disclaimer, the term of this patent is extended or adjusted under 35 U.S.C. 154(b) by 109 days.

(21) Appl. No.: 11/058,654

(22) Filed: Feb. 15, 2005

(65) Prior Publication Data

US 2005/0229675 A1    Oct. 20, 2005

(30) Foreign Application Priority Data

Apr. 20, 2004    (DE) .................. 10 2004 019 008

(51) Int. Cl.
*G01N 27/00* (2006.01)
(52) U.S. Cl. ..................... 73/23.2; 73/31.05
(58) Field of Classification Search ............ 73/23.2, 73/31.05
See application file for complete search history.

(56) References Cited

U.S. PATENT DOCUMENTS

| | | |
|---|---|---|
| 4,163,899 A | 8/1979 | Burough |
| 4,975,582 A | 12/1990 | Mount et al. |
| 5,221,871 A | 6/1993 | Fuchs et al. |
| 5,469,732 A | 11/1995 | Voss .................. 73/31.04 |

FOREIGN PATENT DOCUMENTS

| | | |
|---|---|---|
| DE | 40 30 651 A1 | 4/1992 |
| DE | 43 16 196 A1 | 10/1993 |
| DE | 690 19 569 T2 | 9/1995 |
| DE | 690 31 901 T2 | 8/1998 |
| DE | 101 44 862 A1 | 3/2003 |
| DE | 10159616 A * | 6/2003 |
| DE | 102 45 947 A1 | 4/2004 |
| EP | 0 387 684 A2 | 9/1990 |
| EP | 0 429 397 A2 | 5/1991 |
| GB | 2 262 337 A | 6/1993 |

OTHER PUBLICATIONS

Dakin, J.P. et al.,, "Progress in Liber-Remoted Gas correlation Spectrometry", Optical Engineering, Soc. of Photo-Optical Instrumentation Engineers, Bellingham, US, vol. 31, No. 8, Aug. 1, 1992, pp. 1616-1620, ISSN: 0091-3286m Abstract, figure 2, p. 1616, right column; p. 1617, right column.

* cited by examiner

*Primary Examiner*—Daniel S. Larkin
(74) *Attorney, Agent, or Firm*—McGlew and Tuttle P.C.

(57) ABSTRACT

A gas sensor (1) with a detector element (2), which is specific to a gas to be measured and sends a measured signal that depends on the measured gas concentration, has increased measuring sensitivity for measurements in the concentration range from less than 1 ppb to a few ppb. The detector element (2) is exposed in a gas admission adapter (4) to a gas to be measured via a diaphragm (3) arranged in front of the detector element (2), wherein the gas admission adapter (4) has at least a first opening (20) for the entry of the gas to be measured as well as at least a second opening (30), which is connected with a pressure modulator, which generates periodic gas pressure vibrations in the gas admission adapter (4) and is designed, for example, as a pump (5).

23 Claims, 5 Drawing Sheets

GAS SENSOR WITH INCREASED MEASURING SENSITIVITY

CROSS REFERENCE TO RELATED APPLICATIONS

This application claims the benefit of priority under 35 U.S.C. § 119 of DE 10 2004 019 008.9 filed Apr. 20, 2004, the entire contents of which are incorporated herein by reference.

FIELD OF THE INVENTION

The present invention pertains to a gas sensor, which is specific to a gas to be measured and which sends an electric measured signal that depends on the concentration of the measured gas.

BACKGROUND OF THE INVENTION

Such gas sensors have a detector element, which is specific to the gas to be measured and sends a measured signal that depends on the concentration of the measured gas. In particular, electrochemical gas sensors have been provided with a detector element designed as a measuring electrode that is specific to the gas to be measured. As they are described, for example, in DE 101 44 862 A1, semiconductor sensors with a usually heated ceramic semiconductor element consisting, for example, of $SnO_2$ or an organic polymer semiconductor element, for example, Cu phthalocyanine, as well as catalytic heat tone sensors with a detector element, which is designed as a pellistor (detector bead) and is specific to the gas to be measured, are known. Because of their principle of action, catalytic heat tone sensors are used especially for measuring combustible and explosive gases, for example, methane.

Due to the steadily increasing requirements imposed on the maximum allowable gas concentrations at the workplace and because gases occurring in industry, for example, arsine, are also toxic even in the ppb (parts per billion) range and even at concentrations below 1 ppb, there is an increased need for compact, possibly portable gas sensors, in order to measure specific gas concentrations ranging from a few ppm to below 1 ppb, without having to resort to the very complicated measuring techniques that have hitherto been necessary, for example, mass spectrometry.

SUMMARY OF THE INVENTION

Thus, the object of the present invention is to provide an improved, compact gas sensor with a detector element that is specific of the gas to be measured with increased measuring sensitivity for measurements in the concentration range from below 1 ppb to a few ppb.

According to the invention, a gas sensor is provided with a detector element, which is specific to the gas to be measured. The detector element sends an electric measured signal that depends on the concentration of the measured gas. The detector element is exposed to a gas to be measured, which has gas pressure vibrations generated by means of a pressure modulator.

An essential advantage of the present invention is obtained with the few additional components that are needed to substantially improve the gas sensors of the above noted type, which are known per se, in terms of their measuring sensitivity. The enhanced capabilities as to measuring sensitivity are because it was surprisingly found that the measuring sensitivity of the gas sensors indicated can be substantially increased by periodically generating gas pressure vibrations in the gas space in front of the detector element of the gas sensor at a frequency ranging from a few Hz to a maximum of a few 1,000 Hz and with a pulse and period ranging from a few seconds to a few minutes. The pressure modulator used to generate the gas pressure vibrations (pulses) is preferably a correspondingly driven piezostrictive actuator, a pump, a membrane, a bellows or a pulsed pressurized gas source. Other components are not necessary, in general, so that the gas sensors that are known per se can be made available with substantially improved measuring sensitivity at a relatively low extra cost. The pulse time is determined by the response time of the detector element used in the particular gas sensor. Thus, the response time and consequently the pulse time amount to a few seconds in catalytic heat tone sensors and semiconductor sensors and to a few minutes in electrochemical gas sensors.

The detector element may be exposed to the gas to be measured in a gas admission adapter. Such a gas admission adapter has at least one first opening for admitting the gas to be measured as well as at least one second opening, which is connected with the pressure modulator generating gas pressure vibrations in the gas admission adapter.

The gas sensor may be an electrochemical gas sensor and the detector element may be a measuring electrode, or the gas sensor may be a catalytic heat tone sensor and the detector element may be a pellistor, or that the gas sensor may be a semiconductor sensor and the detector element may be a semiconductor element.

The pressure modulator may be a pump, a membrane, a bellows or a pulsed pressurized gas source. The pressure modulator may be operated periodically at a frequency ranging from a few Hz to a few 1,000 Hz, wherein the pulse time or the period is in the range of a few seconds to a few minutes.

The gas admission adapter may be provided with a material adsorbing interfering components in the gas to be measured. The adsorbing material may be activated carbon, silica gel, granular polyvinyl alcohol or a molecular sieve.

A diaphragm may be arranged upstream of the detector element. The pressure modulator may be designed as a piezostrictive actuator, which is arranged upstream of the diaphragm and cooperates with same. The diaphragm and the detector element may be arranged at spaced locations from one another, so that the inner volume between the diaphragm and the detector element can be modulated in terms of the gas pressure by the piezostrictive actuator.

The material adsorbing interfering components in the gas to be measured, especially activated carbon, silica gel, granular polyvinyl alcohol or a molecular sieve, may be arranged between the diaphragm and the detector element.

The gas sensor may have at least two detector elements for at least two different gases to be measured, wherein each of the at least two detector elements sends a measured signal that is specific to a particular measured gas.

At least one of the openings may be provided with a porous material, especially PTFE (polytetrafluoroethylene), PE (polyethylene) or, a sintered metal, preferably bronze or brass, for the incoming flow of the gas to be measured.

The diaphragm may be designed in the form of a diffusion capillary, which connects two chambers. The gas to be measured flows to the detector element via the first chamber and a gas free from the gas to be measured flows through the second chamber. The second chamber can be induced to vibrate periodically by means of a pressure modulator, so that the gas to be measured can be fed to the detector element in a periodically diluted form, with a modulated measured signal and increased measuring sensitivity. Instead of the chambers with the diffusion capillary, an on-off valve may be arranged upstream of the detector element for periodically feeding a gas, which is free from the measuring gas and is subjected to pressure vibrations, to the gas to be measured.

Exemplary embodiments of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
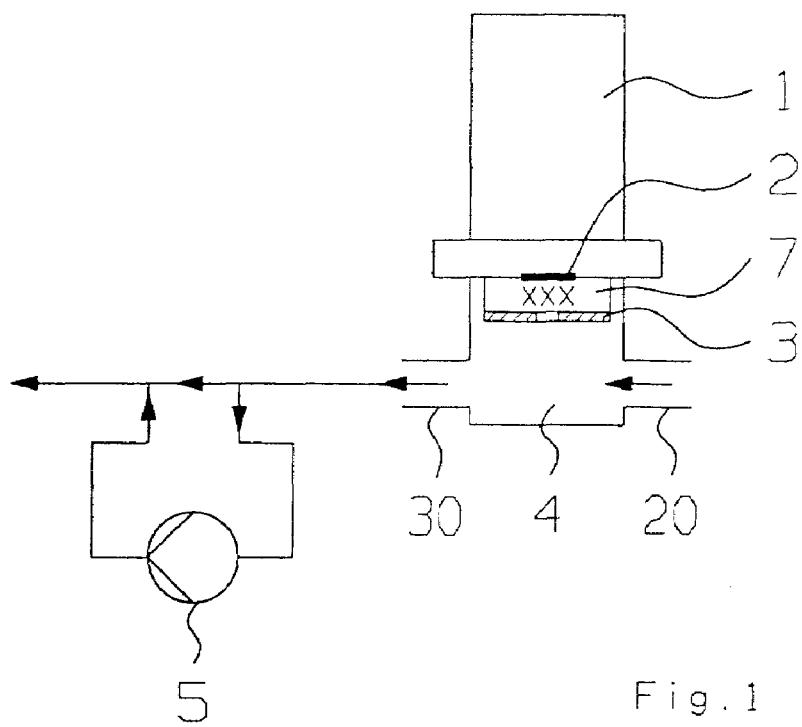
FIG. 1 is a schematic view of a first exemplary embodiment of the present invention.

In the exemplary embodiments, in which the same reference numbers are used for identical components, the gas sensor 1 is schematically shown as an electrochemical gas sensor 1 with a detector element 2 designed as a measuring electrode in these embodiments.

As an alternative, the gas sensor 1 is a catalytic heat tone sensor and the detector element 2 is a pellistor.

The measured signal of electrochemical, amperometric gas sensors 1 is usually a linear function of the concentration of the measured gas in a very broad range of the measured gas concentrations ranging from less than 1 ppb to a few 1,000 ppm (parts per million). The lowest measurable gas concentration is determined downward by the residual current (zero current) of the gas sensor 1, which depends essentially on the temperature and the humidity. Nonstationary temperatures and changes in humidity lead, in particular, to great drifts of the zero current. Cross sensitivities with interfering components (interfering gases) in the measured gas likewise limit the measuring sensitivity or detection sensitivity of electro chemical gas sensors 1.

The electrochemical gas sensor 1 is equipped with a diaphragm 3 arranged upstream of the measuring electrode in the exemplary embodiments. The gas to be measured is reacted at the measuring electrode. The amount of gas to be measured, which is flowing in per unit of time and reaches the measuring electrode, is controlled by means of the diaphragm 3. A stationary measured gas concentration profile becomes established in the orifice of the diaphragm 3. At a predetermined measured gas concentration in the space, the diaphragm 3 completely or at least partially determines the measured sensor current as a function of the particular concrete electrochemical system. It is essential for all exemplary embodiments that the gas space in front of the detector element 2 and/or in front of the diaphragm 3 is periodically induced to have pulses in pressure, gas vibrations or gas pressure vibrations at a frequency ranging from a few Hz to a few 100 Hz, and even up to a few 1,000 Hz in the case of the piezostrictive actuator 25 (FIG. 6) in order to modulate the concentration profile in the diaphragm 3. A markedly larger amount of gas to be measured can thus reach the measuring electrode per unit of time than in the case of a concentration profile set stationarily. The zero current of the gas sensor 1 is not affected by the pressure vibrations. The pressure vibrations are generated periodically, and the pulse time or the period ranges from a few seconds to a few minutes. The zero current of the gas sensor can be eliminated by calculating the sensor current, i.e., the measured signal, in the presence of pressure vibrations with the sensor current without pressure vibrations. This measuring method also functions in the case of drifting zero currents, because the time constant of the zero current drift is several times greater than the time constant or the period of the measured signal modulation.

According to FIG. 1, the gas pressure vibrations are generated by means of a pump 5 with stroke based delivery, which is connected to a second opening 30 of a gas admission adapter 4 and pumps in a closed circuit only, in the example. The pump 5 does generate pressure vibrations in front of the diaphragm 3 in the gas admission adapter 4. The pump 5 is switched on and off periodically. With the pump 5 switched on, the measured signal of the gas sensor 1 increases, depending on the gas to be measured, by a few multiples of 10% to a few multiples of 100% relative to the measured signal obtained with the pump 5 switched off. The gas admission adapter 4 is opened toward the environment via the first opening 20.

Figure 2:
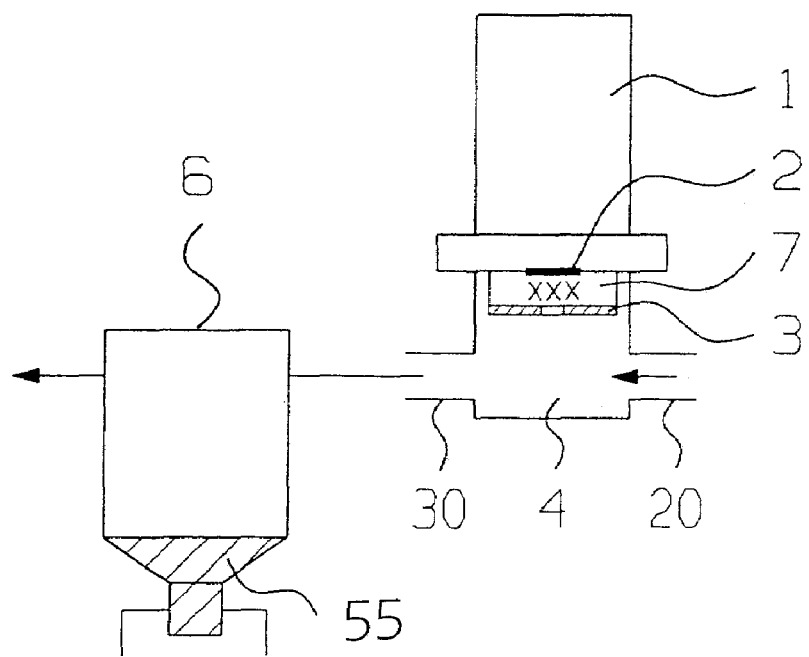
FIG. 2 is a schematic view of a second exemplary embodiment of the present invention.

According to FIG. 2, the gas pressure vibrations are generated by means of an electromagnetically driven membrane 55 e.g., a loudspeaker, with a pressure chamber 6 belonging to it, which is likewise connected with the gas admission adapter 4 via the second opening 30.

Figure 3:
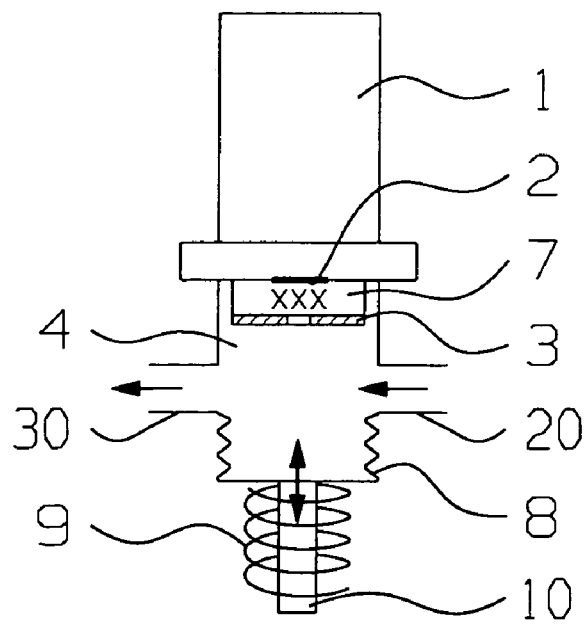
FIG. 3 is a schematic view of a third exemplary embodiment of the present invention.
Figure 4:
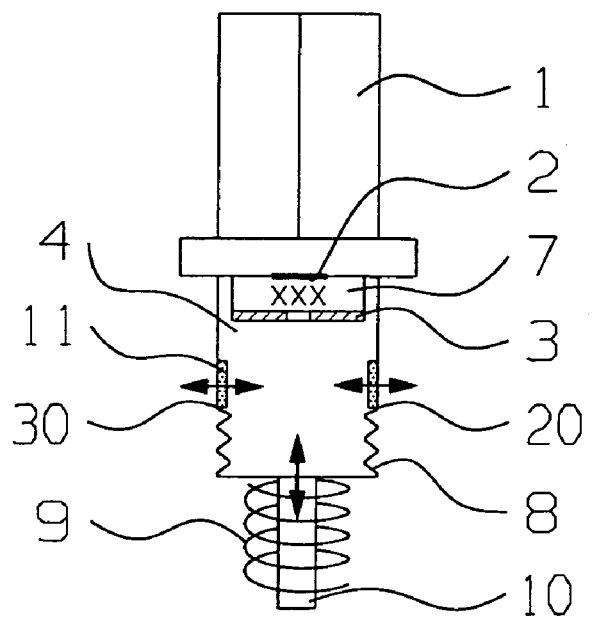
FIG. 4 is a schematic view of a fourth exemplary embodiment of the present invention.

The pressure vibrations are generated in the embodiments of FIGS. 3 and 4 by means of a bellows 8, which is pressurized and released by means of a coil 9 and a magnet 10.

The measured gas flow represented by arrows is affected or determined by selecting the size of the openings 20, 30 and the corresponding flow resistances of the gas admission adapter 4.

In FIG. 4, the openings 20, 30 of the gas admission adapter 4 are filled out with windows 11 made, for example, of porous PTFE for the controlled influx of the gas to be measured.

The increase in the measuring sensitivity is preferably accompanied by an increase in the selectivity of detection of the gas to be measured. This is achieved especially due to an adsorbent material 7, which is arranged between the diaphragm 3 and the detector element 2 in the figures and also smooths the concentration of interfering components from the gas to be measured by adsorption and desorption processes in the course of the pressure vibrations, so that an interfering current that is constant over time, for example, an oxidation current, is generated at the measuring electrode, i.e., at the detector element 2, during corresponding electrochemical reactions taking place at the measuring electrode, i.e., at the detector element 2. Together with the zero current of the gas sensor 1, the interfering signal, which is constant over time, can be separated by calculation by forming the difference at the time of the evaluation of the amplitude of the measured signal, because the measured signal modulation is caused essentially by the gas to be measured only.

Figure 5:
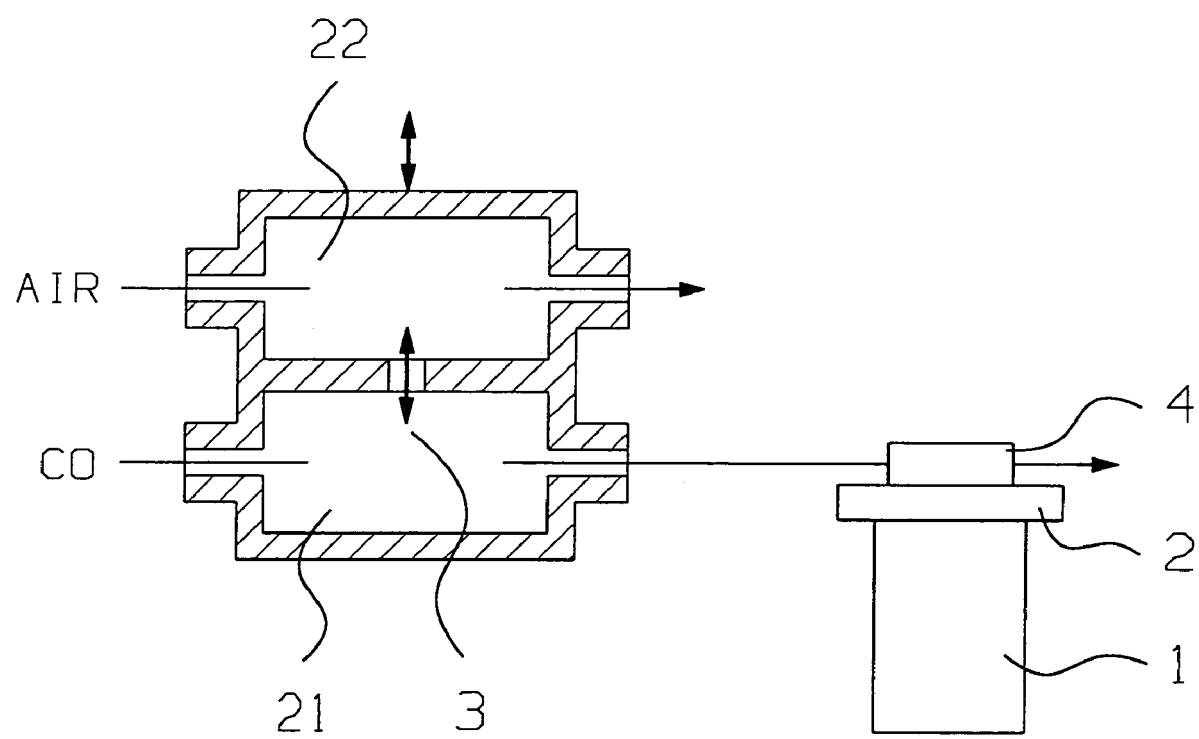
FIG. 5 is a schematic view of a fifth exemplary embodiment of the present invention.
Figure 7:
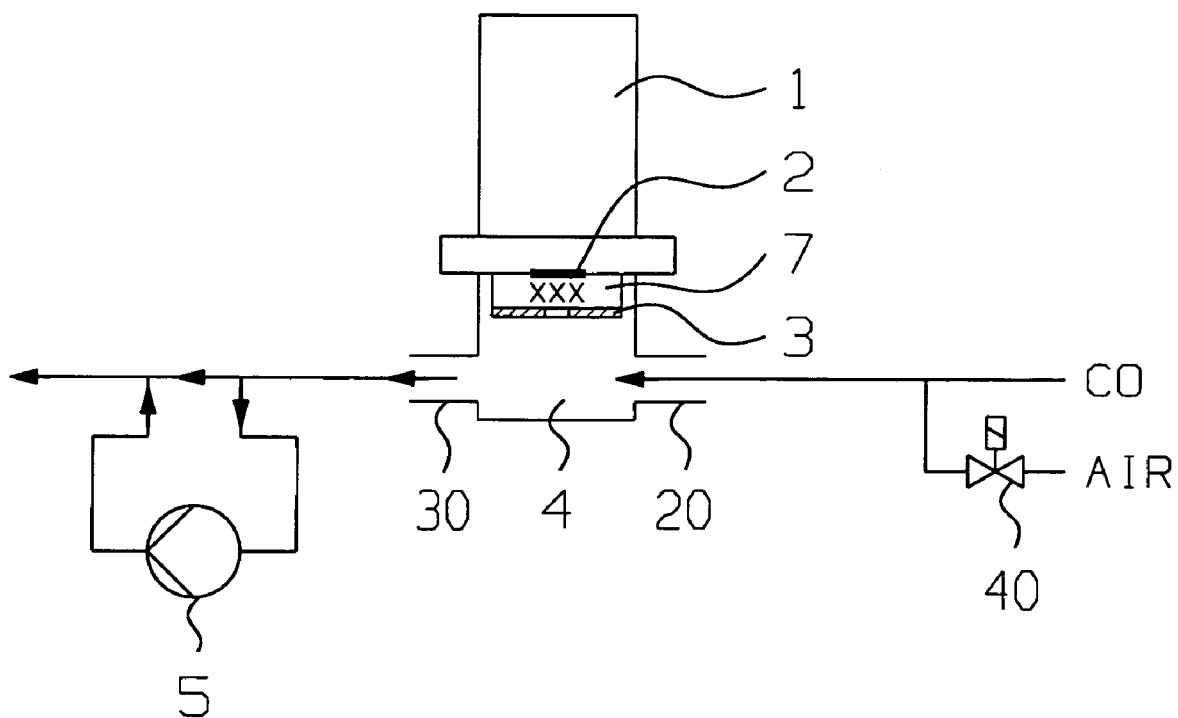
FIG. 7 is a schematic view of a seventh exemplary embodiment of the present invention.

FIG. 5 schematically shows a fifth exemplary embodiment of a gas sensor 1 with a pressure vibration-controlled modulator arranged upstream for the gas to be measured, here CO. Two separate chambers 21, 22 are connected by a diaphragm 3 designed as a diffusion capillary only, the gas to be measured, for example, CO, flowing to the detector element 2 via the first chamber 21 and a gas free from gas to be measured, for example, compressed air (AIR), flowing through the second chamber 22. The second chamber 22 is induced to perform mechanical vibrations ranging in frequency from, e.g., a few Hz to a few 100 Hz by means of a pressure modulator, as is indicated by the double arrows. As a result, the gas to be measured is sent to the detector element 2 through the diaphragm 3 in a periodically diluted form. A modulated measured signal is generated there, whose drift-dependent zero current can be removed by forming the difference in order to obtain an increased measuring sensitivity. This arrangement can also be embodied by means of additional on-off valves which are known per se. As shown in FIG. 7, instead of the chambers 21, 22 with the diffusion capillary, an on-off valve 40 is arranged upstream of the detector element for periodically feeding a gas, which is free from measuring gas and is subjected to pressure vibrations, to the gas to be measured. The on-off valve 40 provides air modulation to the gas to be measured (e.g., CO). A downstream pump 5 is provided for transporting the gas mixture through the sensor as in the embodiment of FIG. 1. In the arrangement being presented here, the valve may be arranged, for example, downstream of a pyrolysis oven in order to modulate the concentration of the pyrolysis products and thus to make possible the detection of the measured gas in the ppb range.

Figure 6:
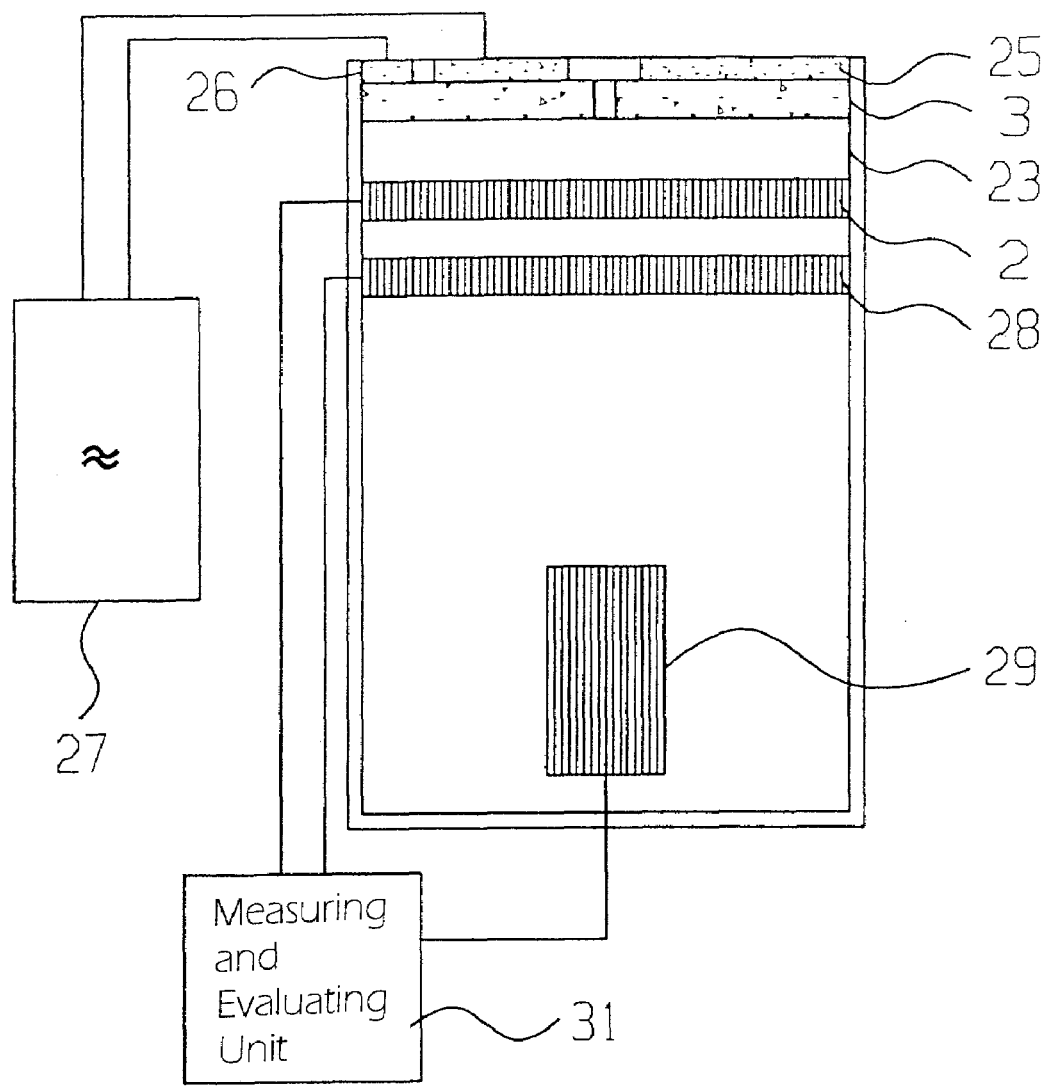
FIG. 6 is a schematic view of a sixth exemplary embodiment of the present invention.

FIG. 6 schematically shows another exemplary embodiment with the essential components of an electrochemical gas sensor in a housing. The pressure modulator is designed as a piezostrictive actuator 25, which is arranged in front of the diaphragm 3 with a central opening and is mechanically connected with same or is preferably mounted on the diaphragm 3. The inner volume 23 between the diaphragm 3 and the detector element 2 is thus periodically subjected in terms of the gas pressure to a vibration frequency ranging from a few Hz to a few 1,000 Hz by the piezostrictive actuator 25. The pulse time and the period is in the range of a few seconds to minutes. Instead of the outer volume in front of the diaphragm 3, it is advantageously possible due to this arrangement to modulate in terms of the gas pressure the inner volume 23 between the detector element 2 and the diaphragm 3, which is usually smaller by several orders of magnitude.

The following advantages arise in this manner:
substantially lower electric and/or mechanical output is necessary for the modulation than in case of the use of pumps;
piezostrictive actuators fail due to wear substantially less frequently than pumps or other moving components;
in case of modulation of the inner volume preset at a fixed value, the modulation frequency can be set once and for all at the time of manufacture of the gas sensor within the framework of the tolerance determined by the manufacturing dispersions; and
the design integration of a piezomechanically excited diaphragm in the gas sensor can be designed such that the connection lines are led to the side facing away from the diaphragm, so that the possibility of plugging in the gas sensor, which is necessary in many practical applications, is achieved.

According to FIG. 6, the piezoelectric actuator 25 is consequently mechanically coupled with the diaphragm 3. The drawings show an optional feedback via a piezo element 26, which acts as a microphone. This technique has been known from piezo buzzers. The feedback to the driver circuit 27 of the piezostrictive actuator 25 makes it possible to set the vibration excitation frequency to the resonant frequency. The electrochemical gas sensor being shown here as an example also contains, besides the detector element 2 designed as a measuring electrode, an auxiliary electrode 28 and a counterelectrode 29, which are actuated and measured by a measuring and evaluating unit 31 with potentiostats. As an alternative, the driver circuit 27 may also be combined with the measuring and evaluating unit 31 with potentiostats or integrated in same.

While specific embodiments of the invention have been shown and described in detail to illustrate the application of the principles of the invention, it will be understood that the invention may be embodied otherwise without departing from such principles.

What is claimed is:

1. A gas sensor arrangement comprising:
a gas sensor with a detector element which is specific to a gas to be measured and which generates an electric measured signal that depends on the concentration of the gas to be measured, said gas sensor defining a space directly exposed to the gas to be measured; and
a pressure modulator generating changes in gas pressure in the gas to be measured, said detector element being directly exposed to the gas be measured.

2. A gas sensor arrangement in accordance with claim 1, wherein said gas sensor further comprises a gas admission adapter wherein said detector element is directly exposed to the gas to be measured in said gas admission adapter, said gas admission adapter having at least one first opening for admitting the gas to be measured as well as at least one second opening connected with the pressure modulator generating gas pressure vibrations in the gas admission adapter.

3. A gas sensor arrangement in accordance with claim 2, wherein the gas admission adapter is provided with a material adsorbing interfering components in the gas to be measured.

4. A gas sensor arrangement in accordance with claim 3, wherein the adsorbing material is activated carbon, silica gel, granular polyvinyl alcohol or a molecular sieve.

5. A gas sensor arrangement in accordance with claim 2, wherein at least one of said openings is provided with a porous material.

6. A gas sensor arrangement in accordance with claim 5, wherein said porous material is one of PTFE (polytetrafluoroethylene), PE (polyethylene), a sintered bronze, a sintered brass and a sintered metal for the incoming flow of the gas to be measured.

7. A gas sensor arrangement in accordance with claim 1, wherein the gas sensor comprises one of an electrochemical gas sensor with said detector element comprising a measuring electrode, a catalytic heat tone sensor with said detector element comprising a pellistor, and a semiconductor sensor with said detector element comprising a semiconductor element.

8. A gas sensor arrangement in accordance with claim 1, wherein said pressure modulator is a pump.

9. A gas sensor arrangement in accordance with claim 1, wherein the pressure modulator is operated periodically at a frequency ranging from 1 Hz to 1,000 Hz, wherein the pulse time or the period is in the range of seconds to minutes.

10. A gas sensor arrangement in accordance with claim 1, wherein a diaphragm is arranged upstream of the detector element.

11. A gas sensor arrangement in accordance with claim 10, wherein the pressure modulator comprises a piezostrictive actuator arranged upstream of the diaphragm and cooperating with said diaphragm, wherein the diaphragm and the detector element are arranged at spaced locations from one another, so that the inner volume between the diaphragm and the detector element can be modulated in terms of the gas pressure by the piezostrictive actuator.

12. A gas sensor arrangement in accordance with claim 10, further comprising a material adsorbing interfering components in the gas to be measured, said material comprising at least one of activated carbon, silica gel, granular polyvinyl alcohol and a molecular sieve, said material being arranged between said diaphragm and said detector element.

13. A gas sensor arrangement in accordance with claim 10, wherein the diaphragm is designed in the form of a diffusion capillary, which connects two chambers, wherein the gas to be measured flows to the detector element via the first chamber and a gas free from the gas to be measured flows through the second chamber, wherein the second chamber can be induced to vibrate periodically by means of a pressure modulator, so that the gas to be measured can be fed to the detector element in a periodically diluted form, with a modulated measured signal and increased measuring sensitivity.

14. A gas sensor arrangement in accordance with claim 1, further comprising another detector element, said detector element and said another detector element being for at least two different gases to be measured, wherein each of said detector element and said another detector element send a measured signal each that is specific of a particular measured gas.

15. A gas sensor arrangement in accordance with claim 1, wherein an on-off valve is arranged upstream of the detector element for periodically feeding a gas, which is free from the measuring gas and is subjected to pressure vibrations, to the gas to be measured.

16. A gas sensor arrangement in accordance with claim 1, wherein said pressure modulator is a pulsed pressurized gas source.

17. A gas sensor arrangement in accordance with claim 1, wherein said pressure modulator is a membrane or a bellows.

18. A gas sensor arrangement, the gas sensor arrangement comprising:
a gas sensor with a detector element which is specific to a gas to be measured and which generates an electric measured signal that depends on the concentration of the measured gas; and
a pressure modulator generating gas pressure vibrations in the gas to which said detector element is exposed and is to be measured; and
a gas admission adapter cooperating with said gas sensor to form a space receiving the gas to be measured, said gas admission adapter having a first opening for admitting the gas to be measured as well as at least one second opening connected with the pressure modulator generating gas pressure vibrations in the gas admission adapter, said detector element being directly exposed to the gas to be measured in said space.

19. A gas sensor arrangement in accordance with claim 18, wherein said gas sensor comprises one of an electrochemical gas sensor with said detector element comprising a measuring electrode, a catalytic heat tone sensor with said detector element comprising a pellistor, and a semiconductor sensor with said detector element comprising a semiconductor element.

20. A gas sensor arrangement in accordance with claim 18, wherein said pressure modulator comprises one of a pump, a membrane, a bellows, a pulsed pressurized gas source or a valve for periodically feeding a gas, which is free from the measuring gas and is subjected to pressure vibrations.

21. A gas sensor arrangement in accordance with claim 18, wherein the gas admission adapter is provided with a material adsorbing interfering components wherein said adsorbing material is one of activated carbon, silica gel, granular polyvinyl alcohol or a molecular sieve.

22. A gas sensor arrangement, the gas sensor arrangement comprising:
a gas sensor with a detector element which is specific to a gas to be measured and which generates an electric measured signal that depends on the concentration of the measured gas; and
a pressure modulator generating gas pressure in the gas to which said detector element is exposed and is to be measured, said gas sensor comprising one of:
an electrochemical gas sensor with said detector element comprising a measuring electrode;
a catalytic heat tone sensor with said detector element comprising a pellistor; and
a semiconductor sensor with said detector element comprising a semiconuctor element.

23. A gas sensor arrangement, the gas sensor arrangement comprising:
a gas sensor with a detector element which is specific to a gas to be measured and which generates an electric measured signal that depends on the concentration of the measured gas;
a pressure modulator generating gas pressure in the gas to which said detector element is exposed and is to be measured; and
a gas admission adapter having at least one first opening for admitting the gas to be measured as well as at least one second opening connected with the pressure modulator generating gas pressure vibrations in the gas admission adapter, said detector element being exposed to the gas to be measured in said gas admission adapter, said admission adapter being provided with an absorbing material adsorbing interfering components wherein said adsorbing material is one of activated carbon, silica gel, granular polyvinyl alcohol or a molecular sieve.

* * * * *